(12) United States Patent
Olson

(10) Patent No.: US 7,658,745 B2
(45) Date of Patent: Feb. 9, 2010

(54) EAR CLEANING DEVICE WITH AN INTEGRAL BULBOUS END

(76) Inventor: Richard C. Olson, 28965 Lemon Rd., Mundelein, IL (US) 60060-9605

( * ) Notice: Subject to any disclaimer, the term of this patent is extended or adjusted under 35 U.S.C. 154(b) by 813 days.

(21) Appl. No.: 10/960,204

(22) Filed: Oct. 7, 2004

(65) Prior Publication Data
US 2005/0096678 A1 May 5, 2005

Related U.S. Application Data

(63) Continuation-in-part of application No. 10/369,915, filed on Feb. 20, 2003, now Pat. No. 7,074,230.

(60) Provisional application No. 60/357,816, filed on Feb. 21, 2002, provisional application No. 60/511,011, filed on Oct. 14, 2003.

(51) Int. Cl.
A61F 11/00 (2006.01)
(52) U.S. Cl. .................................... 606/162
(58) Field of Classification Search ................ 606/162, 606/161; D24/133, 147, 146; 604/1–3
See application file for complete search history.

(56) References Cited

U.S. PATENT DOCUMENTS

| 651,395 | A |   | 6/1900 | Stapp |   |
|---|---|---|---|---|---|
| 3,099,263 | A |   | 7/1963 | Palazzolo |   |
| 3,203,418 | A |   | 8/1965 | Johnston |   |
| D327,322 | S | * | 6/1992 | Brewer, Jr. | D24/147 |
| 5,334,212 | A |   | 8/1994 | Karell |   |
| 5,374,276 | A | * | 12/1994 | Lay | 606/162 |
| 5,509,921 | A |   | 4/1996 | Karell |   |
| 5,632,756 | A |   | 5/1997 | Kruglick |   |
| 5,715,850 | A |   | 2/1998 | Markgraaf |   |
| 5,888,199 | A |   | 3/1999 | Karell et al. |   |
| 5,897,568 | A | * | 4/1999 | Vanraes | 606/162 |
| 6,033,417 | A | * | 3/2000 | Tseng | 606/162 |
| 2001/0001828 | A1 |   | 5/2001 | Begun |   |

* cited by examiner

Primary Examiner—Todd E Manahan
Assistant Examiner—Eric Blatt
(74) Attorney, Agent, or Firm—Fitch, Even, Tabin & Flannery

(57) ABSTRACT

A disposable ear cleaning device having a one-piece, plastic body with an integral scoop at one end having a bowl portion having a smooth lower surface on the bowl. Openings may be formed in the bottom of the bowl for scraping wax and debris from the ear. The preferred openings are parallel slots. The preferred bowl has rounded, upper edges at the rim for scraping ear wax with the front, distal end at a lower height than a rear end of the bowl which is joined to a handle. The preferred handle may be fluted for gripping and turning the bowl when scraping ear wax. A flexible neck may join the bowl to the handle. A bulbous end of plastic or of cotton may be provided at the end of the device opposite the bowl. The referred cleaning device weighs less than one gram and is inexpensive.

10 Claims, 4 Drawing Sheets

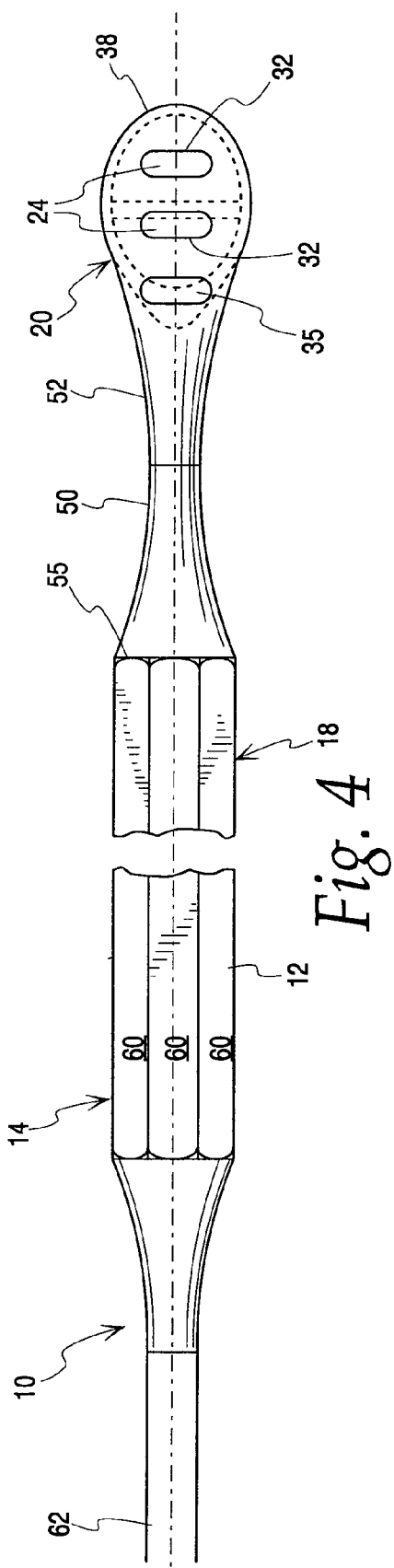
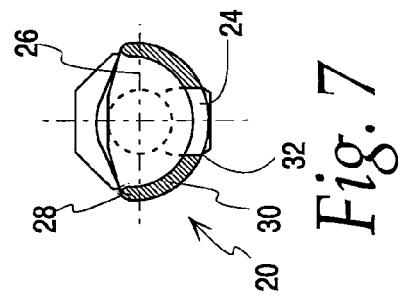
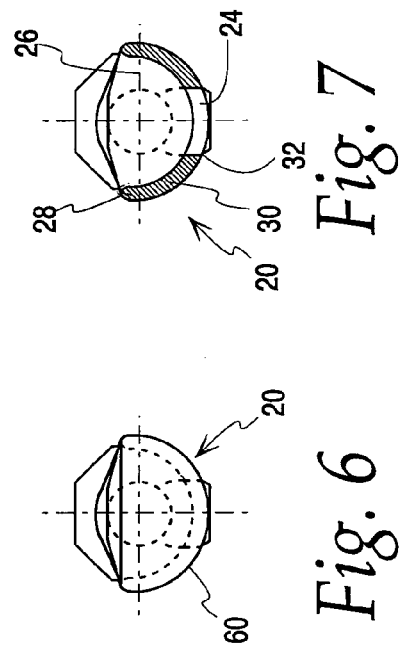
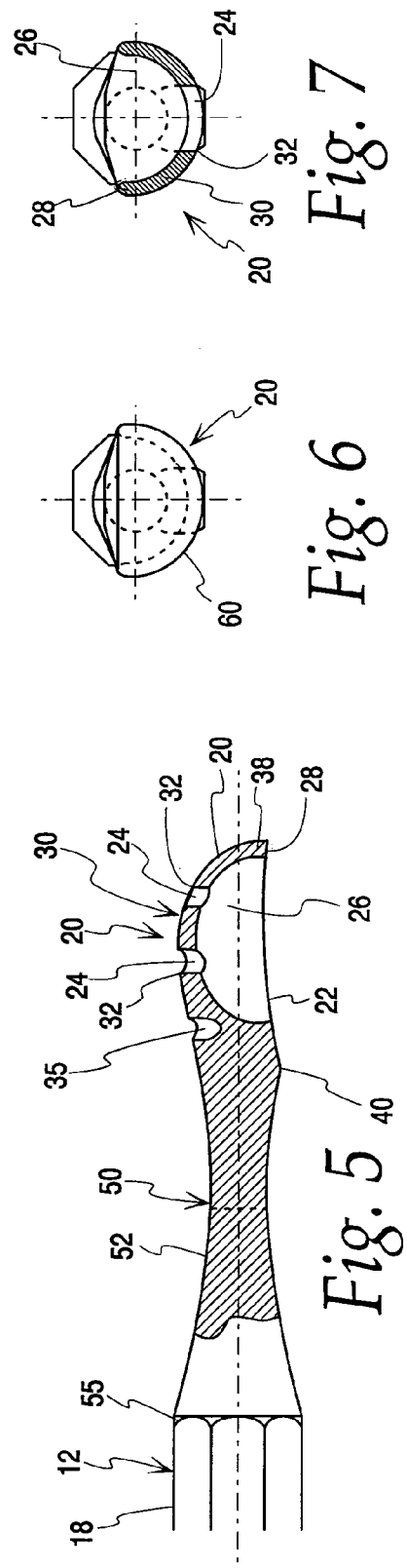

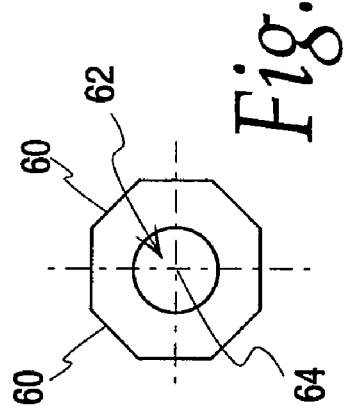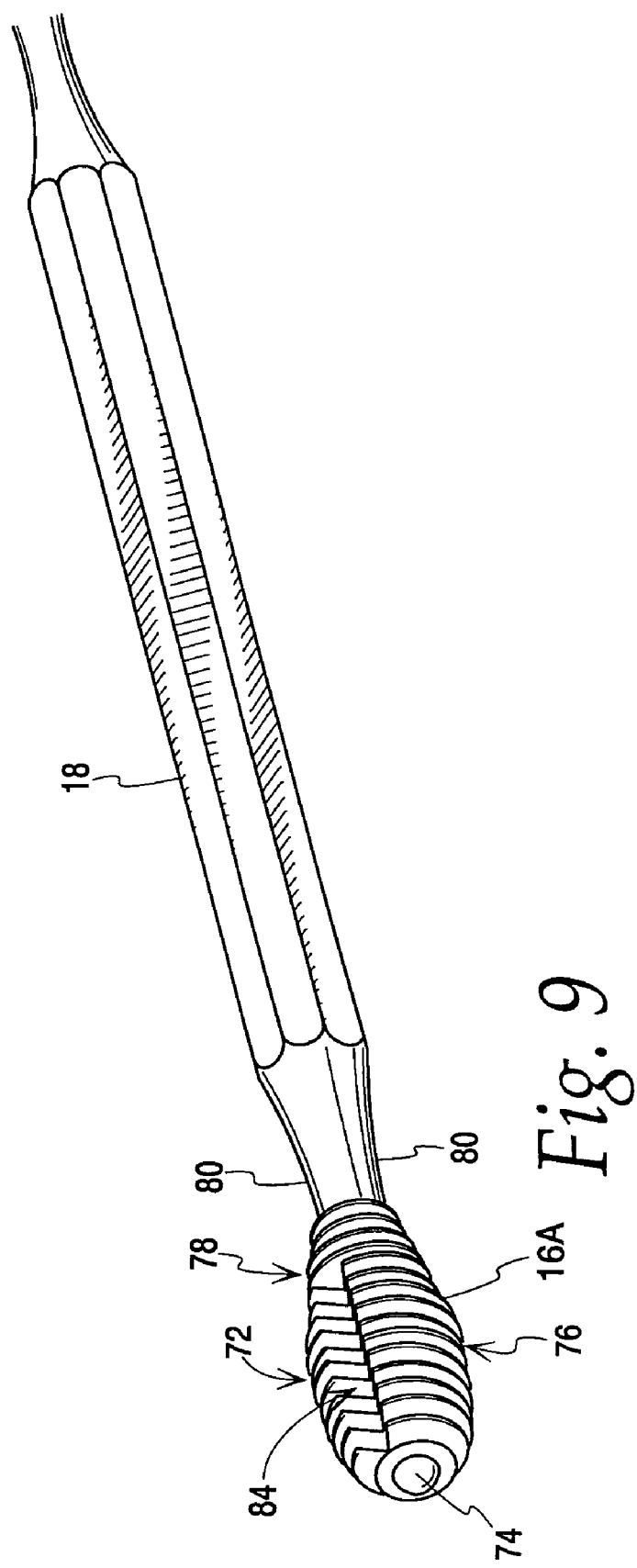

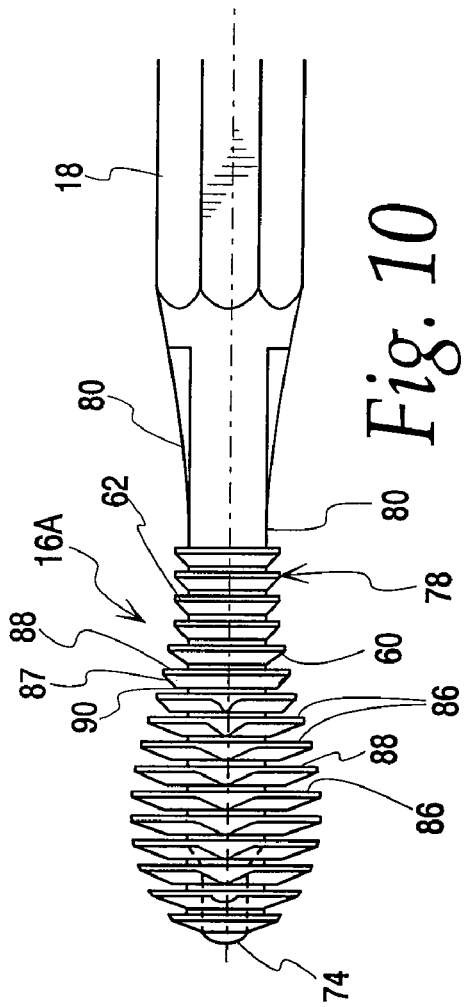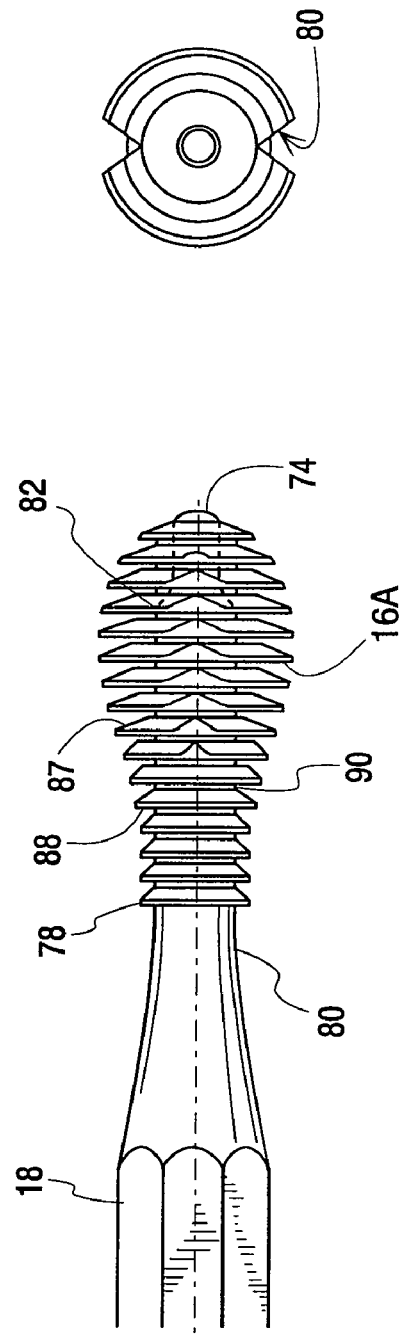

EAR CLEANING DEVICE WITH AN INTEGRAL BULBOUS END

CROSS-REFERENCE TO RELATED APPLICATION

This application is a continuation-in-part of U.S. patent application Ser. No. 10/369,915 filed Feb. 20, 2003, now U.S. Pat. No. 7,074,230 which claims the benefit of U.S. Provisional Application No. 60/357,816; Filed Feb. 21, 2002. This application claims the benefit of U.S. Provisional Patent Application No. 60/511,011, Filed Oct. 14, 2003.

FIELD OF THE INVENTION

This invention relates to a personal, disposable, ear cleaning device which is capable of being used by a person to effectively clean his or her own ears.

BACKGROUND OF THE INVENTION

The most commonly used ear canal hygiene method in use today is a cotton swab which in general works well to remove water and some particulates from the ear but is limited in its design at removing ear wax and excess ear debris. Ear wax and ear debris is actually smeared than removed and may even become more compacted making it more difficult to remove at a later time. The problem with cotton swabs in trying to remove ear wax is that it may actually push the wax deeper into the ear without removing the wax from the surface of the ear.

Various proposals for an ear cleaning device have been made but none of them appear to be commercially available to the consumer except for the one device that is non-disposable and sells for an expensive price, for example, about $5.00 and includes a depth stopper which limits the depth of insertion and has an outer loop or curette with sharp edges to scrape the wax from the ear. This stopper type of ear cleaning device having a curette is shown in U.S. Pat. Nos. 5,509,921; 5,888,199; 5,334,212; and 5,715,850. The problem with such a permanent, expensive ear cleaning device is that it needs to be cleaned and there is always a danger ineffective cleaning and subsequent cutting and a consequent infection. Additionally, the consumers are accustomed to having inexpensive, disposable instruments for which they pay a small price, rather than an expensive implement for cleaning their ears, which, in turn, has to be cleaned.

U.S. Pat. No. 5,374,276 discloses the use of a cotton swab for cleaning the auditory canal and the cotton swab is removed and discarded from the ear cleaning device which is intended to be reused. The consumer is expected to wrap and secure a cotton swab around the spiral hatch pattern on the one end of the handle portion of the ear wax remover. An extraction head on this ear wax remover comprises three similarly shaped projections extending radially outward from a shank. Each projection has the shape of a frustum of a cone. That is, the extraction head comprises three frustum cone shapes portions on the tip of the device. Thus, the ear wax remover tool is to be used over and over again with subsequent swab attachments after each usage.

Thus there is a need for a new and improved ear wax cleaning device, which is small, light-weight, readily disposable and has a more effective ear wax cleaning head, which is not in the form of a curette, but which is made with smooth edges and has an effective ear wax and debris collecting portion.

SUMMARY OF THE INVENTION

In accordance with the preferred embodiment, there is provided a new and improved one-piece, disposable ear cleaning device that effectively removes and collects excess wax and debris from the ear canal area to insure healthy and clean ear hygiene. This is achieved by a one-piece, disposable ear cleaning device of relatively light-weight and which is formed with a spoon or bowl-shaped scoop having rounded edges for cleaning the ear. One embodiment has openings with edges on the outer surface of the bowl for also collecting ear wax or debris. With fingertip control the user can operate the handle portion of the ear cleaning device to use either the edges about the rounded edges of the scoop or to use the back bowl surface openings to gently scrape or remove the debris from the ear and ear canal. Thus there is a dual manner of collecting ear wax and debris and there is provided a very smooth bowl surface for sliding along the ear canal without cutting the ear as the collecting edges scrape and remove the debris.

In the preferred embodiment, the outer edge front, distal of the bowl is lower than the inner rear edge of the bowl to provide a downward slope to the rounded side edges on the top of the bowl for scraping ear wax into the interior of the bowl. Preferably the ear cleaning device has the bowl attached by a flexible neck portion to the handle so that the bowl may flex and conform to the ear canal without scraping or damaging the same as the bowl slides along the surface of the ear.

In accordance with another embodiment, an integral plastic bulbous end is provided on the end of the ear cleaning device opposite the bowl-shaped end for any additional clean up after use of the bowl-shaped end and this bulbous end could be used as an applicator for an ear cleaning solution. In the illustrated embodiment, the bulbous end is tapered with an enlarged diameter central portion and is formed with spaced ribs to collect debris or ear wax in the spaces between the ribs. Thus, a plastic ear cleaning device may be molded in one piece to reduce the cost thereof.

In accordance with another embodiment, the ear cleaning device may be provided with a cotton swab on an end of the handle opposite the bowl. The cotton swab is used to assist in any additional cleanup after use of the bowl and also could be used as an applicator for an ear cleaning solution. In this embodiment, the cotton swab is not to be reused and is disposable along with the ear cleaning device which is made of a very small amount of plastic, for example, several devices to an ounce so that the entire ear cleaning device may be disposed of quickly.

By way of illustration only, the illustrated ear cleaning device is only about 3¼ inches in length and is only about 3/16 inch in width at the handle and that the bulbous end portion having the bowl-shaped scoop. Also, in this illustrated and preferred embodiment the openings on the bottom side of the smooth bowl comprise a pair of parallel openings or slots extending into the interior of the bowl and through which slots the ear collected ear wax or debris may pass for collection. A third, closed slot may also be provided inward of the parallel open slots for debris removal.

BRIEF DESCRIPTION OF THE DRAWINGS

The illustrated embodiment is shown in the attached drawings in which:

FIG. 4 is a bottom view of the ear cleaning device of FIG. 1;

FIG. 5 is a cross-sectional view taken along the line 5-5 of FIG. 2;

FIG. 6 is an end elevational view of the ear cleaning device of FIG. 3;

FIG. 7 is a cross-sectional view taken substantially along the line 7-7 of FIG. 3;

FIG. 8 is an opposite end view of the ear cleaning device from that of FIG. 3;

FIG. 9 is a perspective view of another embodiment having an integral bulbous end molded on the end opposite the bowl-shaped end;

FIG. 10 is an elevational view of the integral bulbous end of the embodiment shown in FIG. 9;

FIG. 11 is an end view of the bulbous end of the cleaning device shown in FIG. 10; and FIG. 12 is a side view of the bulbous end of the cleaning device shown in FIG. 10.

DETAILED DESCRIPTION OF THE PREFERRED EMBODIMENT

Figure 1:
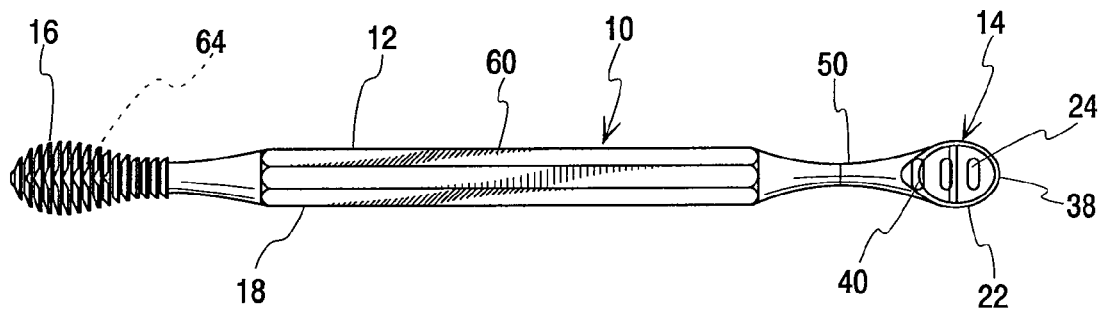
FIG. 1 is a perspective view of a ear cleaning device constructed in accordance with one embodiment of the invention.

As shown in the drawings for purposes of illustration, the illustrated ear cleaning device 10 comprises a main plastic body portion 12 having a bowl or spoon 14 and in this embodiment shown in FIG. 1 having a cotton swab 16 at the opposite end of a handle portion 18 which extends between the bowl or spoon 14 and a bulbous end 16 of cotton or a bulbous end 16a of plastic integrally molded a the time of molding the ear cleaning device 10.

Figure 2:
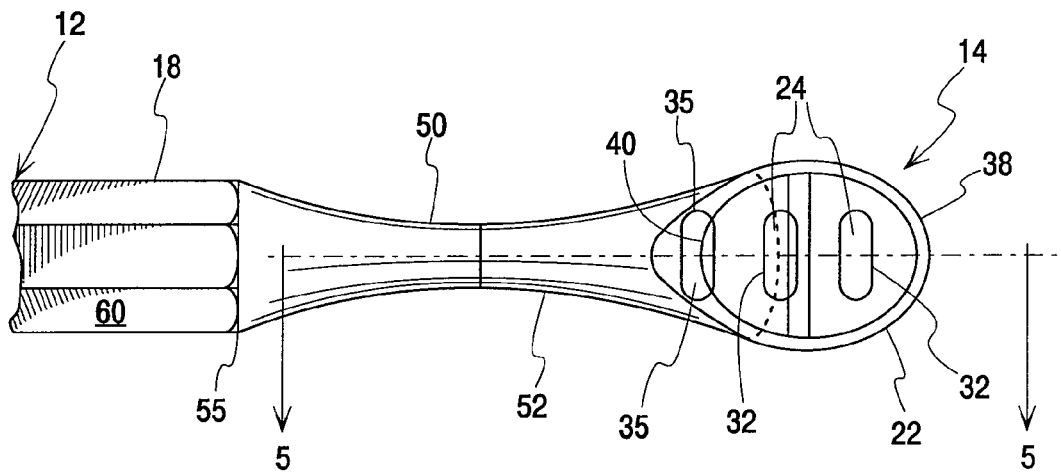
FIG. 2 is an enlarged plan view of the ear cleaning device of FIG. 1.

In accordance with the illustrated embodiment of the invention as best seen in FIGS. 2 and 5, the bowl 14 includes a rounded bowl or bulbous-shaped portion 20 that is integral with the body portion 12 of the ear cleaning device and has smooth rounded outer, upper side, edges 22 and ear cleaning openings 24 in the bowl portion for scraping and collecting ear wax or ear debris within a hollow interior 26 of the bowl. As best seen in FIG. 5, the edges 22 have a rounded radius 28 so that they will not scrape the ear with a sharp edge when collecting ear wax. Likewise the rear surface 30 of the bulbous portion having the openings 24 is also smooth and has rounded edges defining a slot or opening projecting inwardly into the hollow interior 26. The tool bowl is smooth to slide along the ear with the backside surface 30 of the bowl smoothly sliding along the ear and any wax will be caught by an edge 32 of an opening 24 to scrape and remove the ear wax will then pass through the opening 24.

In the illustrated embodiment of the invention, there is a pair of parallel openings 24 in the form of parallel slots as best seen in FIGS. 2 and 5. In addition, it is preferred that there is a third closed slot 35 which can also collect or scrape ear wax as the tool is being pulled backwardly in the ear. The third slot is optional. Manifestly, the number of openings 24, 35 and the size and shape of the openings may be varied from the illustrated embodiment having the parallel slots which seem to work quite well when using this smooth the rounded outer bowl portion to collect wax rather than the rounded top side edges 22 at the top of the bowl.

Figure 3:
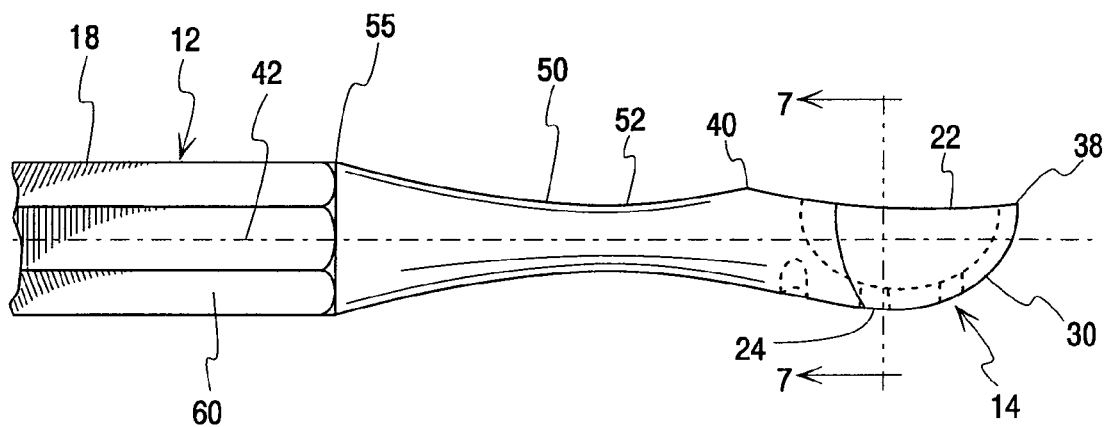
FIG. 3 is an enlarged side-elevational view of the ear cleaning device of FIG. 1.

Also in accordance with the invention, as best seen in FIGS. 3 and 5, it is preferred to have the front tip or distal end 38 of the bowl be at a lower height than the rearward end 40 of the bowl as shown in FIGS. 3 and 5. By way of example only, the height or distance of the forward edge 38 from the axis center line 42 of the ear cleaning tool is in this instance is about 0.031 whereas the opposite highest point at the inner rear end 40, the scoop or bowl is about 0.060. Also, byway of example only, the top curved surface of the bowl is curved along an upward and rearwardly radius portion that is at a radius of 0.908 inch.

In accordance with another aspect of the illustrated embodiment, the handle portion 18 is joined to the bowl 14 by a flexible neck portion 50 on the body 12. Herein the portion is made with a reduced cross-sectional thickness. By way of example only, the neck portion at its smallest cross-section is less than one-half of the cross-sectional thickness of the handle. Herein the cross-sectional thickness of the neck is also curved along curved surfaces 52 as shown in FIGS. 2, 3, 4 and 5. The neck is curved on the opposite sides to gradually reduce the cross-sectional thickness between a junction point 55 with the handle and the upper rear end 40 of the bowl.

To provide a good gripping surface in order to be able to rotate the ear cleaning device without slipping, it is preferred to provide elongated flutes 60, herein there are eight flutes on the handle. The flutes are elongated, flat surfaces on the outer surface of the handle. Obviously, the shape of the flutes and the number of flutes can be different from that described herein. In the embodiments of FIGS. 1-8, the bulbous end 16 is in the form of a cotton swab 16 as shown in FIG. 1; which is attached to a cylindrical plastic end 62 on the end of the handle opposite the bowl 14. The cotton swab may be made of cotton and have a bulbous-shape which projects outwardly beyond the distal end 64 of the ear cleaning plastic body 12. As stated earlier the use of the cotton swab is optional and some ear cleaning devices may be provided without the cotton swab while others may not be provided with the cotton swab or may be provided with the integral plastic bulbous end 16a.

In operation, the user will insert the scoop-shaped end or bowl into the ear and gently scrape with the rim, outer top edges 28 of the bowl which are rounded at a radius 38 to allow a general scraping action as the handle is twisted while holding onto the flutes 60 between the fingers. In an embodiment not illustrated, the bowl lacks any openings 24, 35 on the rear surface of the bowl and only the rim edges are used to scrape ear wax and debris. In the illustrated embodiment, a forward or backward axial movement of the device will allow the rear surface of the bowl to use the openings 24 on the underside of the bowl and the backward motion will be able to use the closed slot 35 to collect ear wax. The excess wax and debris will be moved into the openings 24 and into the hollow potion 26 and collected.

In another embodiment, which is illustrated in FIGS. 9, 10 and 11, the bulbous cotton swab 16 has been replaced with an integral, plastic bulbous end 16a with spaced portions 70 preferably in the form of flexible ribs 72.

The bulbous end 16a is for cleaning and massaging the entrance to the ear canal and other ear-surfaces. With fingertip control, the user can operate this bulbous end of the device to scrape and collect wax and excess debris from or around the ear and ear canal. The user does this by rubbing the ear surface in an "in & out" or "up & down" motion. This motion causes the flexible ribs 72 to scrape and then fill with earwax and debris. This debris is collected in the grooved ribs and removed safely from the ear. The user also gets an additional benefit by using this same end to gently massage the ear for personal comfort.

The main bulbous end 16a has a tapered distal end 74, a larger and more rigid middle section 76 and a tapered inner end 78 jointed to the central shaft of the ear cleaning device 10. Preferably, the bulbous plastic end 16a is sized and formed in the shape of a common cotton swab and is ribbed from one end to the other end. The ribbed inner end 78 is connected to the main shaft at a reduced cross-section portion 80 resulting in a flexible connection giving the user safety in use. The bulbous round end 16a is formed with eased or rounded rib edges 82 and is designed to be of soft, flexible plastic to insure additional safety and comfort to the user. Additionally, the ribbed bulbous end also has two V-grooves 84 molded through the ribs 72, the V opposite the other V. These grooves are molded through the ribs to create a continuous vent. This vent is to "insure" the user cannot create a seal within the ear between the device and the ear canal walls. If the seal were allowed to occur, this would create a vacuum within the person's ear canal resulting in a potential injury.

Referring now in greater detail to the ribs 72, they are formed with varying diameters with the largest diameter ribs being at the middle section and gradually reducing in circumference and diameter toward the distal end 74 and inner end 78. Herein, the ribs are spaced by equal open spaces 86 between adjacent ribs. The ribs preferably have an inclined or tapered, outer surface 87 between a larger diameter wall 88 and a smaller diameter wall 90. The spaces 86 are donut-shaped between the inner central shaft portion and respective adjacent large diameter wall 88 of one rib and a smaller diameter wall 90 of an adjacent rib.

The preferred ear cleaning device is molded to be relatively soft and flexible so as not to be so rigid as to scrape or damage the user's ear. A blend of plastic such as about 60 percent (60%) low density polyethylene and 40 percent (40%) high density polyethylene has been found to give the desired softness. Manifestly, other manners of achieving this softness may be used.

Thus, it will be seen that the one piece plastic device 10a of the second embodiment need not have a secondary operation of attaching a cotton swab 16 to the plastic end as in the first embodiment. Hence, the second embodiment with integral, plastic bulb end may be less expensive to manufacture than the first embodiment.

Although preferred embodiments have been described, it is to be understood that other non-illustrated embodiments may fall within the purview of the appended claims.

What is claimed is:

1. A disposable ear cleaning device comprising:
    a one piece integral body;
    a central handle portion of the body to be gripped by the user;
    an integral scooper for removing ear wax at one end of the body;
    an integral bulbous end at an opposite end of the body; and
    the integral bulbous end comprises a central shaft portion having a largest diameter section at a proximal end of the integral bulbous end and a smallest diameter section at a distal end of the integral bulbous end, and a plurality of spaced annular ribs extending radially from the central shaft portion at least at the largest and smallest diameter sections to an outer annular edge extending generally perpendicular to the longitudinal axis of the shaft, the annular ribs varying in radial diameter along the shaft.

2. An ear cleaning device in accordance with claim 1 wherein the plurality of spaced ribs includes a middle section with the largest radial diameter ribs positioned within the middle section.

3. An ear cleaning device in accordance with claim 2 wherein the ribs gradually decrease in radial diameter as their distance from the middle section increases.

4. A disposable ear cleaning device in accordance with claim 3 wherein at least two of the plurality of ribs decrease in radial diameter.

5. An ear cleaning device in accordance with claim 1 wherein the spaced ribs are aligned along the central shaft portion such that the plurality of spaced annular ribs form a bulbous shape similar to a cotton swab.

6. A disposable ear cleaning device in accordance with claim 1 comprising: a body made of a mixture of about sixty percent (60%) low
    density polyethylene and forty percent (40%) high density polyethylene.

7. A disposable ear device in accordance with claim 1 wherein a vent is defined by grooves formed in adjacent ribs of the plurality of spaced annular ribs which extends longitudinally along at least a portion of the integral bulbous end.

8. A disposable ear cleaning device comprising:
    a one piece body;
    a handle of the body to be grasp by the user;
    an integral scoop for removing ear wax at one end of the body;
    an integral bulbous end at an opposite end of the body wherein the integral bulbous end comprises a series of ribs which extend radially from the body; and
    a vent defined by grooves formed in adjacent ribs which extends longitudinally along at least a portion of the integral bulbous end.

9. An ear cleaning device in accordance with claim 8 wherein the body has a reduced cross-section intermediate the handle and the bulbous end portion to provide a flexible connection therebetween.

10. An ear cleaning device in accordance with claim 8 wherein the body varies in diameter along at least a portion of the integral bulbous end.

* * * * *

UNITED STATES PATENT AND TRADEMARK OFFICE
CERTIFICATE OF CORRECTION

PATENT NO. : 7,658,745 B2  Page 1 of 1
APPLICATION NO. : 10/960204
DATED : February 9, 2010
INVENTOR(S) : Richard C. Olson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1209 days.

Signed and Sealed this

Thirtieth Day of November, 2010

David J. Kappos
*Director of the United States Patent and Trademark Office*